United States Patent [19]

Salzburg et al.

[11] Patent Number: 5,587,511
[45] Date of Patent: Dec. 24, 1996

[54] PROCESS FOR OBTAINING ADIPIC ACID

[75] Inventors: Herbert Salzburg, Leichlingen; Georg Steinhoff, Krefeld; Andreas Gosch, Bochum; Gerd Hufen, Duisburg, all of Germany

[73] Assignee: Bayer Aktiengesellschaft, Leverkusen, Germany

[21] Appl. No.: 556,572

[22] Filed: Nov. 13, 1995

[30] Foreign Application Priority Data

Nov. 18, 1994 [DE] Germany ............ 44 41 175.8

[51] Int. Cl.$^6$ .................................. C07C 51/00
[52] U.S. Cl. .......................... 562/513; 562/593
[58] Field of Search .................. 562/513, 593

[56] References Cited

U.S. PATENT DOCUMENTS

| | | | |
|---|---|---|---|
| 3,818,081 | 6/1974 | Adamek | 260/537 P |
| 4,014,903 | 3/1977 | Moore | 260/345.9 |
| 4,146,730 | 3/1979 | Nishikido et al. | 562/513 |
| 4,254,283 | 3/1981 | Mock | 562/530 |
| 4,442,303 | 4/1984 | Mims | 560/191 |

FOREIGN PATENT DOCUMENTS 033851  8/1981  European Pat. Off. .

*Primary Examiner*—Samuel Barts
*Attorney, Agent, or Firm*—Joseph C. Gil; Richard E. L. Henderson

[57]  ABSTRACT

The present invention relates to a process for obtaining adipic acid from the aqueous nitric acid mother liquors that arise during industrial adipic acid production by (i) removing nitric acid from the aqueous mother liquor by evaporation to a concentrate having a residual content of at most about 2.5 wt. % of $HNO_3$, (ii) mixing the concentrate obtained according to step (i) with water or dilute aqueous nitric acid in a quantity corresponding to a weight ratio of solid to liquid of about 1:2.1 to about 1:1.2, (iii) allowing the water added in step (ii) or the nitric acid added in step (ii) to act upon the concentrate for at least about 10 minutes at about 20° to about 80° C., and (iv) separating adipic acid as crystals that are formed (1) during step (iii) at temperatures of no more than about 35° C. or (2) after step (iii) by cooling the mixture from step (iii) to about 10° to about 35° C.

4 Claims, No Drawings

PROCESS FOR OBTAINING ADIPIC ACID

BACKGROUND OF THE INVENTION

This invention relates to a process for obtaining adipic acid from the by-product stream ("mother liquor") arising from the oxidation of technical mixtures of cyclohexanol/cyclohexanone using nitric acid and isolation of the principal quantity of adipic acid by crystallization, in which the acids remaining in the stated mother liquor are obtained as a mixture ("technical glutaric acid").

During the production of adipic acid by oxidation of cyclohexanol and/or cyclohexanone, in particular of technical mixtures of cyclohexanol and/or cyclohexanone using nitric acid, glutaric acid and succinic acid are formed as by-products. These by-products accumulate in the adipic acid crystallization mother liquor. A proportion of this mother liquor is thus discharged from the process in order to prevent by-product accumulation. Once nitric acid and water have been separated from this mother liquor, the remaining dicarboxylic acid mixture may be worked up by distillation to yield "technical glutaric acid". The resultant distillation residue contains predominantly adipic acid and carbonization products, together with metallic catalysts such as copper or vanadium.

The adipic acid contained in the dicarboxylic acid mixture (approximately 25 to 45 wt. %) is effectively lost as adipic acid, reduces the quality of the technical glutaric acid obtained, consequently impairing its suitability for use in the tanning material sector, and increases the amount of the distillation residue when the glutaric acid is worked up by distillation.

A series of processes has thus been developed to recover adipic acid. According to U.S. Pat. No. 4,146,730, addition products, which may be separated from the adipic acid, are formed from glutaric and succinic acid on the one hand and urea on the other. U.S. Pat. No. 3,818,081 describes the conversion of glutaric and succinic acid into the imides and the separation thereof from the adipic acid. According to European Patent Application 33,851, glutaric and succinic acid are converted by reaction with alkylamines into the corresponding amides, which may in turn be separated from the adipic acid. U.S. Pat. No. 4,442,303 discloses esterification of the dicarboxylic acids and separation of the acids in the form of their esters. U.S. Pat. No. 4,014,903 discloses simple cooling crystallization to recover adipic acid from the by-product discharge stream. However, the efficiency of such a process remains unsatisfactory for an industrial process because the quantity of adipic acid that may be obtained in this manner is small and, in particular, because (as is also confirmed in U.S. Pat. No. 4,254,283) much succinic acid is crystallized out together with the adipic acid, such that a further stage is necessary for the purpose of separating these two acids. As disclosed in U.S. Pat. No. 4,254,283, this further stage may, for example, proceed by converting the succinic acid into succinic anhydride which is then separated from the adipic acid by distillation.

The object of the present invention was thus to provide a novel process for the recovery of the adipic acid present in the acidic mother liquor, which, in comparison with the stated prior art processes, may be performed in a simple manner and yet yields adipic acid or "technical glutaric acid" of a comparatively elevated purity. This object could be achieved by means of the process according to the invention which is described in greater detail below.

SUMMARY OF THE INVENTION

The present invention relates to a process for obtaining adipic acid from aqueous nitric acid mother liquors that arise during industrial adipic acid production, said mother liquor containing about 2 to about 8 wt. % of succinic acid, about 4 to about 10 wt. % of glutaric acid, and about 2 to about 25 wt. % of adipic acid and an $HNO_3$ concentration of 40 to 60 wt. % (relative to the aqueous nitric acid without including said succinic, glutaric, and adipic acids), comprising (i) removing nitric acid from the aqueous mother liquor by evaporation to a concentrate having a residual content of at most about 2.5 wt. % of $HNO_3$, relative to the weight of the evaporation residue, (ii) mixing the concentrate obtained in step (i) with water or aqueous nitric acid having an $HNO_3$ content of at most about 10 wt. % in a quantity corresponding to a weight ratio of solid to liquid of about 1:2.1 to about 1:1.2, (iii) allowing the water added in step (ii) or the nitric acid added in step (ii) to act upon the concentrate for a period of at least about 10 minutes at about 20° to about 80° C., optionally with continuous mixing and optionally with at least partial dissolution of the concentrate, and (iv) separating adipic acid as crystals from the liquid phase of step (iii) (said liquid phase containing glutaric acid), said crystals of adipic acid being formed either (1) during step (iii) when temperatures in step (iii) are no more than about 35° C. or (2) after step (iii) when temperatures in step (iii) are greater than about 35° C. by cooling the mixture from step (iii) to about 10° to about 35° C.

DETAILED DESCRIPTION OF THE INVENTION

The starting material used in the process according to the invention is the above-mentioned mother liquor from industrial production of adipic acid by oxidation of cyclohexanol and/or cyclohexanone, in particular of technical mixtures of cyclohexanol and cyclohexanone by means of nitric acid. The principal quantity of adipic acid produced in this reaction occurs in the form of solid adipic acid that may readily be separated from the reaction mixture. The mother liquor constituting the starting material of the process according to the invention that remains upon isolation of this solid adipic acid contains the above-stated acids in the above-stated quantities at an $HNO_3$ concentration in the mother liquor, relative to water and $HNO_3$ without including other constituents, of 40 to 60 wt. %. The mother liquor used in the process according to the invention may also contain small concentrations of heavy metal compounds, in particular copper or vanadium compounds such as used as catalysts in the oxidation reaction. The total concentration of these contaminants, relative to the total weight of the mother liquor, is generally at most 1 wt. %. Other, unidentified contaminants causing discoloration may also be present in the mother liquor.

In step (i) of the process according to the invention, nitric acid and water are first removed from the mother liquor by evaporation down to a residual content of at most about 2.5 wt. % (preferably at most 1.2 wt. %) of $HNO_3$.

In step (ii) of the process according to the invention, the concentrate obtained in step (i) is mixed with water or aqueous nitric acid having an $HNO_3$ concentration of up to about 10 wt. % (preferably up to 3 wt. %), where the quantity of water or of dilute nitric acid is calculated to provide a weight ratio of concentrate solids to liquid of 1:2.1 to 1:1.2 (preferably 1:1.8 to 1:1.3).

During phase (iii) of the process according to the invention, the water or dilute nitric acid is allowed to act upon the concentrate within the temperature range of 20° to 80° C. (preferably of 23° to 70° C.) for a period of at least 10 minutes (preferably at least 30 minutes). This "action" is preferably supported by at least occasional mixing, particularly by at least occasional stirring of the mixture.

Step (iv) of the process according to the invention involves separating solid crystals from the mixture present after phase (iii) at a temperature of about 10° to about 35° C. (preferably of 23° to 30° C.). Thus, the mixture obtained according to step (iii), which generally comprises a solution at the relatively elevated temperatures within the stated range for step (iii), must be cooled to a temperature within the stated range for step (iv) if the treatment according to step (iii) was performed at a temperature above 35° C. However, if the treatment according to step (iii) proceeded within the temperature range specified for step (iv), cooling is not necessary, and steps (iii) and (iv) would thus involve mixing the concentrate with the water or dilute nitric acid at a maximum temperature of 35° C. (preferably of 30° C.) and subsequently isolating the acid crystals present. The acid crystals may, for example, be isolated by centrifugation or filtration. The total duration of the action of water or acid according to step (iii) and the optionally performed cooling, which is preferably performed gradually, is generally about 10 minutes to about 5 hours (preferably 30 to 90 minutes).

The crystalline acid separated according to step (iv) is a technical adipic acid having an adipic acid content of at least 80 wt. % and also still contains residual quantities of glutaric and succinic acid. This first product of the process according to the invention may, for example, be returned to the adipic acid production process and, for example, mixed into the reaction mixture leaving the oxidation reactor.

The mother liquor present after isolation of the technical adipic acid according to step (iv) is an acid mixture containing about 40 to about 70 wt. % of glutaric acid, about 10 to about 30 wt. % of adipic acid, and about 20 to about 40 wt. % of succinic acid. This "technical glutaric acid" may be isolated in substantially anhydrous form by evaporating this mother liquor (i.e., in an optional step (v) of the process according to the invention) and constitutes the second product of the process according to the invention. This "technical glutaric acid" may, for example, be used as an auxiliary in the leather industry (e.g., for tanning or dyeing).

When performing the process according to the invention, care is preferably taken to ensure, to the extent possible, that the products of the process are colorless and freed from heavy metals. Traces of heavy metals are preferably removed by ion-exchange treatment, which is generally performed at about 10° to about 135° C. Ion-exchangers suitable for this purpose are, for example, acidic cationic ion exchange resins based on polystyrenes having sulfonic acid groups, such as LEWATIT® resins distributed by Bayer AG.

Other contaminants are preferably removed by activated carbon treatment, which is also generally performed at about 10° to about 135° C., at any desired point in the overall process.

It would thus be possible, for example, to subject the concentrate present upon completion of step (i) to the specified purification processes as a melt at about 80° to about 135° C. (preferably 90° to 120° C.) or, alternatively, to subject the aqueous mother liquor arising from step (iv) at about 10° to about 80° C. (preferably at 40° to 65° C.) to the specified purification processes.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

The mother liquor concentrates used in the following Examples 1 to 7 and 12 to 15 were obtained by evaporation of mother liquors from industrial adipic acid production and have a residual $HNO_3$ content of below 0.7 wt. %, a succinic acid content of 20 to 25%, a glutaric acid content of 33 to 37%, and an adipic acid content of 36 to 42%. These concentrates were mixed with dilute nitric acid of the concentration stated below and heated to 70° C. while being dissolved. Solutions having the solids content stated below were obtained at this temperature. After 5 minutes' stirring at 70° C., the temperature was reduced over a period of approximately 90 minutes to 30° C. and the crystalline adipic acid was filtered out. The resultant filtrate substantially consisted of an aqueous, nitro-acid solution of "technical glutaric acid" of the composition stated in the following table.

| Example | $HNO_3$ (%) | Solids[1] (%) | AA[2] in solids (%) | AA in C[3] (%) | AA yield (%) | TGA[4] Composition (%) | | |
|---|---|---|---|---|---|---|---|---|
| | | | | | | AA[5] | GA[6] | SA[7] |
| 1 | 5 | 38 | 40 | 90.2 | 70.3 | 17.8 | 49.1 | 33.1 |
| 2 | 2 | 42.6 | 40 | 87.1 | 71.2 | 17.1 | 49.5 | 33.4 |
| 3 | 2 | 44 | 42 | 90.7 | 60.1 | 23.6 | 47.6 | 28.8 |
| 4 | 5 | 40 | 36 | 86.9 | 74.1 | 13.5 | 49.0 | 37.5 |
| 5 | 2 | 36 | 42 | 93.7 | 75.0 | 15.7 | 52.0 | 32.3 |
| 6 | 3 | 40 | 40 | 91.1 | 75.2 | 15.0 | 50.6 | 34.4 |
| 7 | 1.5 | 42 | 41 | 84.3 | 74.8 | 19.6 | 53.1 | 27.3 |

[1]solids content of solution (70° C.)
[2]adipic acid (i.e., "AA")
[3]crystalline product ("C")
[4]"technical glutaric acid" (i.e., "TGA")
[5]AA in TGA
[6]glutaric acid in TGA
[7]succinic acid in TGA

Example 8

20 g of a mixture prepared from 40% of adipic acid, 24% of succinic acid, and 36% of glutaric acid together with 1% of Cu (as $Cu(NO_3)_2$) and 1.5% of V (as $V_2O_5$) (i.e., the evaporated mother liquor from the industrial adipic acid production process) was stirred with 3 g of water at 90° C. to 100° C. and then passed into a column heated to 110° C. with a packing of 60 ml of LEWATIT® SP 112.

After an initial run of water, approximately 28.5 g of eluate that had an amber color and contained approximately 12 ppm of Cu together with 2 ppm of V were obtained.

Example 9

The eluate from Example 8 was passed at 37° C. through a column filled with 450 g of activated carbon (2 to 6 mm) and washed through with 250 ml of water at a drop rate of approximately 300 ml/h. The discharged product was colorless. 1900 g of colorless "technical glutaric acid" were obtained by evaporation.

Example 10

The crystallization mother liquor (4.9 g/l Cu, 350 mg/l V) from Example 9 was exchanged in a cation exchanger column (LEWATIT® SP 112 from Bayer AG, 700 ml packing volume) in the $H^+$ form at 50° C. at an exchange speed of approximately 450 ml/h. The introduced quantity was 5282 g and the solids content was 36%. The eluate obtained in individual fractions contained 2.7 to 4.3 ppm of Cu and 3.4 ppm of V.

Example 11

500 g of crude, amber-color, melted "technical glutaric acid", obtained by evaporating the eluate from Example 8, were introduced into a column heated to 140° C. and filled with 49 g of activated carbon. The discharged product was colorless.

Examples 12–15

In the following examples, 100 g portions of solid material (24.9% succinic acid, 35.0% glutaric acid, and 40.0% adipic acid) were stirred together with water at various temperatures (T) for 180 minutes, suction filtered at 30° C. (or 26° C. in example 12), and analyzed for composition.

| Example | T (°C.) | Solids content (%) | Crystalline product SA (%) | Crystalline product GA (%) | Crystalline product AA (%) | TGA SA (%) | TGA GA (%) | TGA AA (%) |
|---|---|---|---|---|---|---|---|---|
| 12 | 26 | 43.5 | 5.4 | 7.4 | 87.1 | 34.0 | 47.9 | 18.1 |
| 13 | 30 | 40.0 | 4.4 | 6.0 | 89.6 | 33.1 | 46.7 | 20.2 |
| 14 | 32 | 40.0 | 4.2 | 6.4 | 89.1 | 33.3 | 46.6 | 20.1 |
| 15 | 80 | 40.0 | 5.8 | 7.7 | 86.5 | 33.6 | 47.4 | 19.0 |

What is claimed is:

1. A process for obtaining adipic acid from the aqueous nitric acid mother liquor that arise during industrial adipic acid production, said mother liquor containing about 2 to about 8 wt. % of succinic acid, about 4 to about 10 wt. % of glutaric acid, and about 2 to about 25 wt. % of adipic acid and an $HNO_3$ concentration of 40 to 60 wt. % (relative to the aqueous nitric acid without including said succinic, glutaric, and adipic acids), comprising (i) removing nitric acid from the aqueous mother liquor by evaporation to a concentrate having a residual content of at most 2.5 wt. % of $HNO_3$, relative to the weight of the evaporation residue, (ii) mixing the concentrate obtained according to step (i) with water or aqueous nitric acid having an $HNO_3$ content of at most 10 wt. % in a quantity corresponding to a weight ratio of solid to liquid of 1:2.1 to 1:1.2, (iii) allowing the water added in step (ii) or the nitric acid added in step (ii) to act upon the concentrate for a period of at least 10 minutes at 20° to 80° C., optionally with continuous mixing and optionally with at least partial dissolution of the concentrate, and (iv) separating adipic acid as crystals from the liquid phase of step (iii), said crystals of adipic acid being formed either (1) during step (iii) when temperatures in step (iii) are no more than about 35° C. or (2) after step (iii) when temperatures in step (iii) are greater than about 35° C. by cooling the mixture from step (iii) to 10° to 35° C.

2. A process according to claim 1 wherein in step (iii) the mixture obtained according to step (ii) is stirred for a period of at least 30 minutes at 23° to 70° C. and in step (iv) the crystalline adipic acid that is present at 23° to 30° C. or the adipic acid that crystallizes out after the mixture has cooled to 30° to 23° C. is removed from the liquid phase.

3. A process according to claim 1 additionally comprising (v) removing water and nitric acid by evaporation from the liquid phase from step (iv) to obtain an acid mixture containing glutaric acid.

4. A process according to claim 1 additionally comprising removing heavy metals and/or other contaminants by treatment at any step with an ion-exchanger and/or activated carbon in solution or as a melt.

* * * * *